United States Patent [19]

Beyar et al.

[11] Patent Number: 5,004,454
[45] Date of Patent: Apr. 2, 1991

[54] AUXILIARY INTRA-URETHRAL MAGNETIC VALVE FOR PERSONS SUFFERING FROM URINARY INCONTINENCE

[75] Inventors: Mordechay Beyar, Caesaria; Amnon Foux, Haifa, both of Israel

[73] Assignee: Technion Research and Development Foundation Ltd., Hiafa, Israel

[21] Appl. No.: 476,211

[22] Filed: Feb. 7, 1990

[30] Foreign Application Priority Data

Feb. 15, 1989 [IL] Israel .................................. 089297

[51] Int. Cl.$^5$ ............................ A61F 2/02; A61F 2/04
[52] U.S. Cl. ........................................ 600/30; 623/11; 623/12; 128/DIG. 25; 251/65
[58] Field of Search ...................... 600/29, 30; 623/11, 623/12; 128/DIG. 25; 251/65

[56] References Cited

U.S. PATENT DOCUMENTS

| | | | |
|---|---|---|---|
| 3,731,670 | 5/1973 | Loe | 600/30 |
| 3,812,841 | 5/1974 | Isaacson | 600/29 |
| 4,121,741 | 10/1978 | Adamson | 251/65 X |
| 4,154,226 | 5/1979 | Hennig et al. | 128/DIG. 25 |
| 4,452,423 | 6/1984 | Beblavi et al. | 251/65 |
| 4,553,533 | 11/1985 | Leighton | 600/30 |

FOREIGN PATENT DOCUMENTS 1194358  6/1970  United Kingdom ....... 128/DIG. 25

Primary Examiner—Ronald Frinks
Attorney, Agent, or Firm—Browdy and Neimark

[57] ABSTRACT

A urethral magnetic valve for insertion into the urethra of a person suffering from incontinence includes a plastic tube of a diameter suitable for insertion close to the bladder. It forms a valve seat in its distal portion to be normally closed by an elongate valve member of a ferro-magnetic, non-corrosive material. The valve member has a surface corresponding to the valve seat at its proximal end, tapers towards its distal end, and is urged onto the seat by a spring attached at its distal end to the proximal valve end. The spring extends inside the tube and is fastened to the latter at its proximal end; it is so dimensioned that it will keep the valve closed at normal pressure and permit the valve member to be lifted off the seat by overpressure in the bladder. The person wishing to urinate holds a permanent or electro-magnet close to the skin over the pubic area, which attracts and tilts the ferro-magnetic valve member, thereby opening the passage through the tube and through the urethra.

6 Claims, 2 Drawing Sheets

AUXILIARY INTRA-URETHRAL MAGNETIC VALVE FOR PERSONS SUFFERING FROM URINARY INCONTINENCE

BACKGROUND OF THE INVENTION

The invention relates to an auxiliary valve to be inserted into the urethra of persons suffering from an inability to control their bladder function so as to enable them to open and to close the valve for the purpose of controlling the flow of urine. It furthermore relates to an auxiliary valve which opens automatically to release urine from the bladder whenever the pressure therein rises above normal maximum pressure, or in all cases where the person suffers from urinary flow obstructions, combined with incontinence.

Many elderly persons of both sexes suffer from incontinence of urine owing to malfunctioning of the sphincter surrounding the urethra or to the person's inability to mobilize the sphincter muscle so as to open or close the outlet from the bladder. This failure is very unpleasant and disturbing, and much research has gone into the development of means to help the sufferers so as to prevent involuntary outflow of urine or to collect it by means of diapers or flexible containers. Up to the present two ways are being employed: surgical implantation of periurethral valves, and pneumatically operated valves inserted into the urethra by means of a transurethral guide.

Both kinds have their inherent drawbacks: —surgery should be avoided as far as possible in the case of elderly debilitated persons, while pneumatic operation of the valves is relatively complicated, as well as raising the cost of the instrument to a height making it too expensive for many persons.

The present invention has, therefore, the object to provide a urethral valve for non-surgical insertion into the urethra of male and female persons alike, which can be operated by the person from the outside by means of a magnetic field, so as to permit urination, whenever it is felt to be necessary.

It is another object to provide such valve in a manner that it opens the urinary tract as soon as the pressure in the bladder reaches a predetermined dangerous height.

It is still another object to provide such valve in a shape permitting its ready insertion and withdrawl without general anesthetics.

And it is a final object to provide such valve at low cost by mass production so as to make it available to practically every person suffering from incontinence, or combined with urinary flow obstruction.

SUMMARY OF THE INVENTION

The urethral valve according to the invention consists of a tube of an inert material and an outer diameter suitable for insertion into the urethra of a person without inconveniencing this person. The tube has a proximal end to be positioned close to the bladder and a distal end, and includes a central throughgoing passage containing a coaxial valve seat which is normally closed by a metallic valve member urged upon the seat by a spring means. The valve member is oblong and in concentric alignment with the tube while in closing state, but is adapted to be tilted into angular alignment by means of a magnetic force exerted by a magnet held outside of the body causing parital opening of the passage through the tube by nonclosure of the valve seat by the valve member. The spring is dimensioned so as to prevent lifting the valve member off the valve seat at normal pressure inside the bladder, and to permit its lifting off the valve seat by excessive pressure, which may be predetermined and adjusted by the physician treating the patient. Means are provided for holding the valve in position in the urethra, such as inflatable rubber rings, barbs or the like, all of which are known to the art, and do not prevent removal of the valve by an authorized person.

The valve seat includes a flexible gasket, such as an O-ring, while the valve member is provided with a conical surface cooperating with the gasket from where the member tapers towards its distal end. Its proximal end is in the shape of a concentric bar having a tension spring attached to its end. The other end of the spring is held in position at the proximal end of the tube by means of a transverse pin or by other means.

The valve member consists either of a metal which is attracted by a magnet, or is in the form of a permanent magnet. In the former case the proximal end is in the shape of a very thin pin or needle, serving to straighten the valve member by means of the spring force upon cessation of a magnetic field, while in the case of the member being a permanent magnet, the proximal end may be thickened, whereby the valve member and the thickened end form the two magnetic poles. In the latter case a permanent or electro-magnet held opposite the valve will tilt the member in a more forceful way than without this thicker proximal end.

The urethral valve is inserted into the urethra by a trans urethral guide by means of cooperating screw-threads, and is similarly removed, without any surgery. It will be understood that for persons with a narrow urethra a valve of smaller outer diameter will be selected than for a person having normal dimensions.

SHORT DESCRIPTION OF THE DRAWING

DETAILED DESCRIPTION OF THE DRAWING

Figure 1:
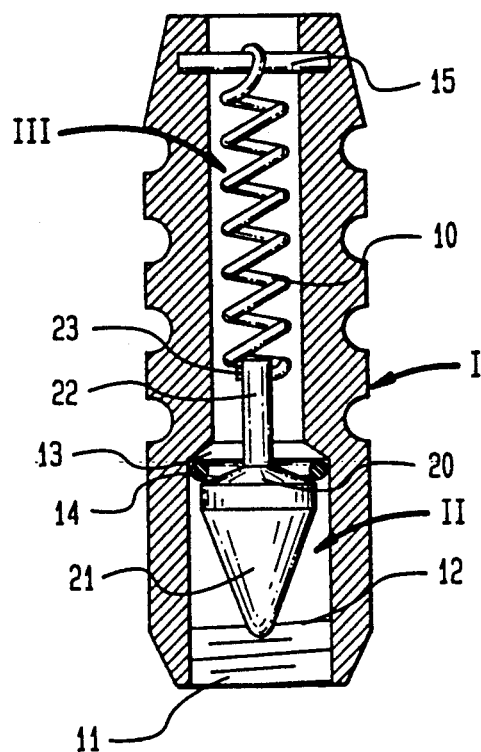
FIG. 1 is a longitudinal section through a valve in closed state.
Figure 2:
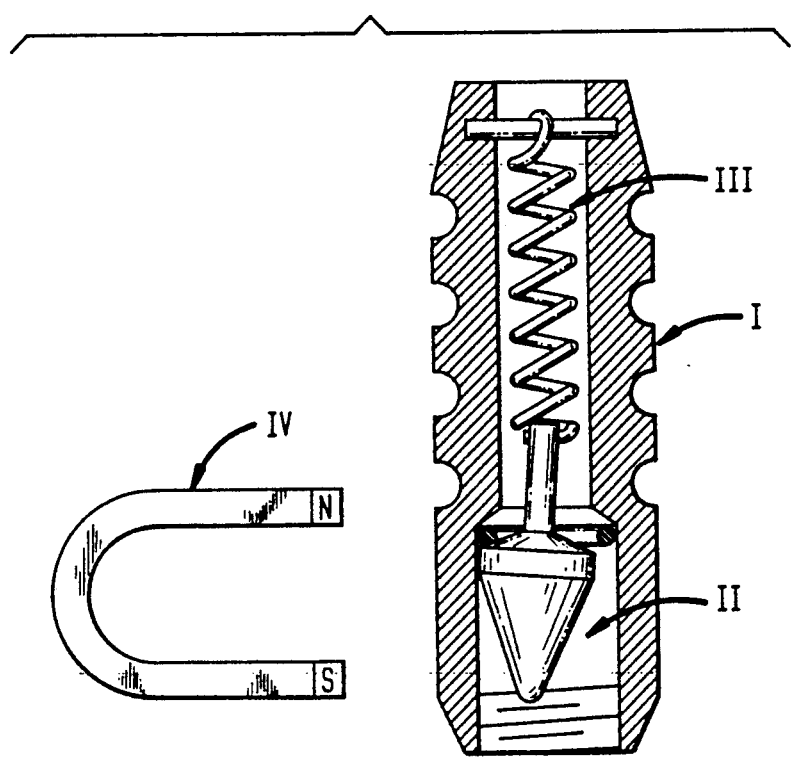
FIG. 2 is a longitudinal section through the valve of FIG. 1 opened by the magnetic field of a permanent magnet held closed to it.

With reference to FIGS. 1 and 2 of the drawing, an embodiment of the urethral valve includes an outer tube I coextensive with the inner diameter of the urethra which is made of an inert material as e.g. polyethylene or polymethacrylate, and is provided with internal screw thread at its distal end for connection to a trans-urethral guide. The tube is centrally perforated by a passage divided into a longer proximal bore 10 of smaller diameter and a longer distal bore 12 of larger diameter which form between them a valve seat 13 of conical configuration. An O-ring 14 of a soft material is positioned on the valve seat to effect tightness of the valve. A valve member II of a ferromagnetic material is inserted into the tube from the distal end and is urged onto the O-ring 14 by means of a spiral tension spring III. The valve member comprises a conical seating surface 20 corresponding to the size of the O-ring and a tapering distal end 21, both extending into the large-diameter bore 12. Its proximal end is in the form of a bar 22 of small diameter having its outer end perforated by a transverse bore 23 serving to accomodate the end of the spring III. The outer end of the spring is secured to the tube I by means of a transverse pin 15. The spring is dimensioned and tensioned so as to withstand a pressure in the bladder of between 0.04 and 0.12 bar. The length of the tube is about 40 mm and its outer diameter varies between 6 and 9 mm, in accordance with its use. The strength of the magnetic field necessary to open the valve, i.e. to tilt the valve member, should be between 100 and 300 gauss.

FIG. 2 shows the valve member tilted towards the left side of the drawing by the magnetic field created by a permanent magnet IV which is positioned at a distance of between 30 to 40 mm from the valve, which corresponds to the distnce of the bladder from the body outside. As can be clearly seen, tilting of the valve member opens a passage between the seating surface 20 and the O-ring 14 through which the urine can escape, emptying the bladder. Removal of the magnet IV effects closing of the valve by means of the spring force which pulls the member II into the position shown in FIG. 1.

Figure 3:
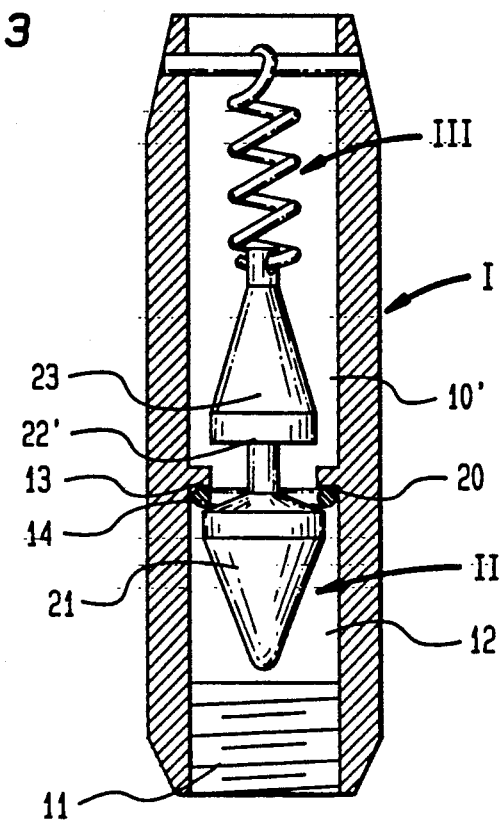
FIG. 3 is a longitudinal section through a urethral valve provided with a valve body of a magnetic material.

The urethral valve illustrated in FIG. 3 is similar to that shown in FIGS. 1 and 2, with the exception that the valve member II is a permanent magnet, provided with two poles which are—in the present case—marked N and S. A horseshoe magnet positioned in front of the valve will tilt the member by either attracting the pole of opposite polarity or repulse the pole of identical polarity. For this purpose both ends, 21 and 22', of the valve member are of larger diameter and are tapering toward their respective ends, whereby the proximal end is attached to a spring III, similar to the aforedescribed embodiment. The proximal bore 10' is of the same or of similar diameter as the distal bore 12, in order to provide sufficient space for tilting of the thicker pole portion 22'. The remaining parts are identical with those of the embodiment shown in FIGS. 1 and 2 and are indexed by the same numerals.

Figure 4:
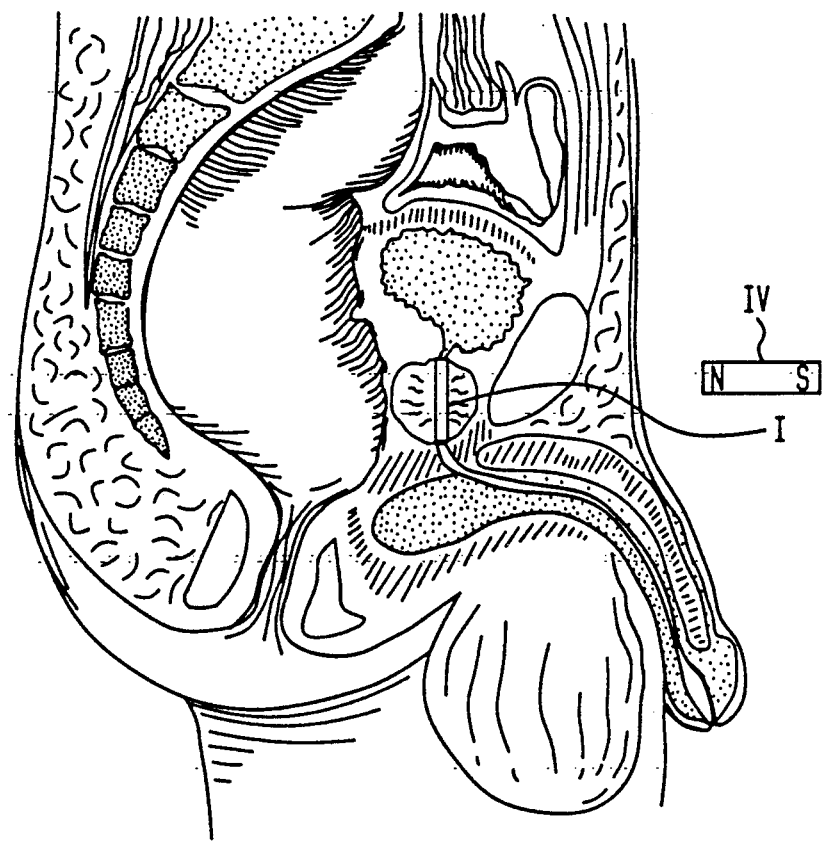
FIG. 4 is a section through the abdomen of a person showing the urethral valve inserted into the proximal end of the urethra.

FIG. 4 is a section through an abdomen of a male person showing a valve I inserted into the urethra close to the bladder. A permanent or electro-magnet IV is shown to be held close to the valve which will open it and enable the person to urinate. In the female body the valve may be positioned in any portion of the urethra.

In patients provided with a urinary diversion, as e.g. a Koch pouch, a urethral valve of the above kind may be inserted therein within the abdominal wall.

It will be understood that the urethral valves shown in the foregoing represent only two embodiments of the invention, and that they may be modified and otherwise designed by a person skilled in the art within the spirit of the invention and the scope of the appended claims.

The casing or tube may be made of any material that is nonmagnetic and sufficiently inert so as not to irritate the tissues and not be rejected by the body. The valve member may be made of any ferromagnetic or magnetic material which will not be corroded or otherwise be changed by contact with urine and other body fluids, suitable materials being certain alloys of stainless steel, or gold-plated metals. The casing in the form of a tube may have a smooth outer surface or may be grooved as shown in FIG. 1. The O-ring positioned on the valve seat may be omitted if the material of the housing is sufficiently soft so as to provide safe closure of the valve. The valve seat as well as the valve member may have other shapes than the cone shown in the drawings, for instance semispherical, as long as good and safe closure is obtainable and the valve member can be suitably tilted by a magnetic field to effect opening of the passage for urine flow.

We claim:

1. An auxiliary urethral valve for insertion into the urethra of a person unable to control his or her bladder function, having a proximal end and a distal end, the valve including a spring-supported, ferromagnetic valve member adapted to be opened by a magnetic field created by a magnet positioned outside the body of the wearer, said valve comprising:

a tubular casing of a diameter coextensive with the dimension of the urethral duct and made of a nonmagnetic and innocuous material, said tube being lengthwise perforated by a throughgoing passage provided with an inwardly protruding valve seat, a valve member of a ferromagnetic, innocuous material comprising a valve surface corresponding to said valve seat of said tubular casing, a solid valve body extending from said valve surface and tapering towards its distal end and a spring-engaging portion extending from said valve body in proximal direction, a tension spring having its distal end fastened to said spring-engaging portion of said valve member and its proximal end fastened to said casing, so dimensioned as to urge said valve member onto said valve seat at normal pressure in the bladder and to permit said valve member to be lifted of said seat by overpressure;

means for opening said valve at normal bladder pressure being effected by tilting of said valve member by a magnetic field, whereby a first portion of said valve surface is lifted off said valve seat and a second portion remains in contact with said valve seat opening a passage for urine from the bladder into the open.

2. The urethral valve of claim 1 comprising a soft gasket positioned on said valve seat.

3. The urethral valve of claim 2 wherein said gasket is in the shape of an O-ring.

4. The urethral valve of claim 1 comprising a magnetic valve member and a spring-engaging portion of a diameter similar to the diameter of said solid valve body, said portion tapering towards the proximal end of said valve.

5. The urethral valve of claim 1, provided at its distal end with internal screw-thread for connection to a trans-urethral guide.

6. The urethral valve of claim 1 wherein said tubular casing is made of polymethacrylate.

* * * * *